(12) United States Patent
Gilmour

(10) Patent No.: US 6,394,117 B1
(45) Date of Patent: May 28, 2002

(54) PLUG FOR CONNECTING TO A WALKER

(75) Inventor: Robert Farrer Gilmour, Auckland (NZ)

(73) Assignee: Bodyworks Properties Limited, Auckland (NZ)

( * ) Notice: Subject to any disclaimer, the term of this patent is extended or adjusted under 35 U.S.C. 154(b) by 0 days.

(21) Appl. No.: 09/401,649

(22) Filed: Sep. 23, 1999

(30) Foreign Application Priority Data

Sep. 23, 1998 (NZ) .................................................. 332002

(51) Int. Cl.7 .................................................. A61H 3/00
(52) U.S. Cl. .......................................... 135/84; 135/67
(58) Field of Search .............................. 135/67, 84, 65, 135/77, 78, 82, 86; 248/188.9, 688, 687; 602/16, 23, 27

(56) References Cited

U.S. PATENT DOCUMENTS

| | | | | | |
|---|---|---|---|---|---|
| 2,453,742 A | * | 11/1948 | Bowen | ......................... | 135/77 |
| 3,007,726 A | * | 11/1961 | Parkin | .......................... | 135/77 |
| 3,163,437 A | * | 12/1964 | Phillipson | ..................... | 135/77 |
| 3,289,685 A | * | 12/1966 | Parker | ........................... | 135/77 |
| 4,947,882 A | * | 8/1990 | Levasseur | ..................... | 135/77 |
| 5,794,638 A | * | 8/1998 | Richey | .......................... | 135/65 |
| 5,954,075 A | * | 9/1999 | Gilmour | ....................... | 135/84 |

* cited by examiner

Primary Examiner—Beth A. Stephan
(74) Attorney, Agent, or Firm—Young & Thompson

(57) ABSTRACT

A plug for a walker. The plug comprises a plate with an aperture therein. A plurality of pins extend from the plate, the pins being positioned to engage in correspondingly positioned apertures in a walker body. The invention includes arms secured to a walker body by use of such a plug.

9 Claims, 2 Drawing Sheets

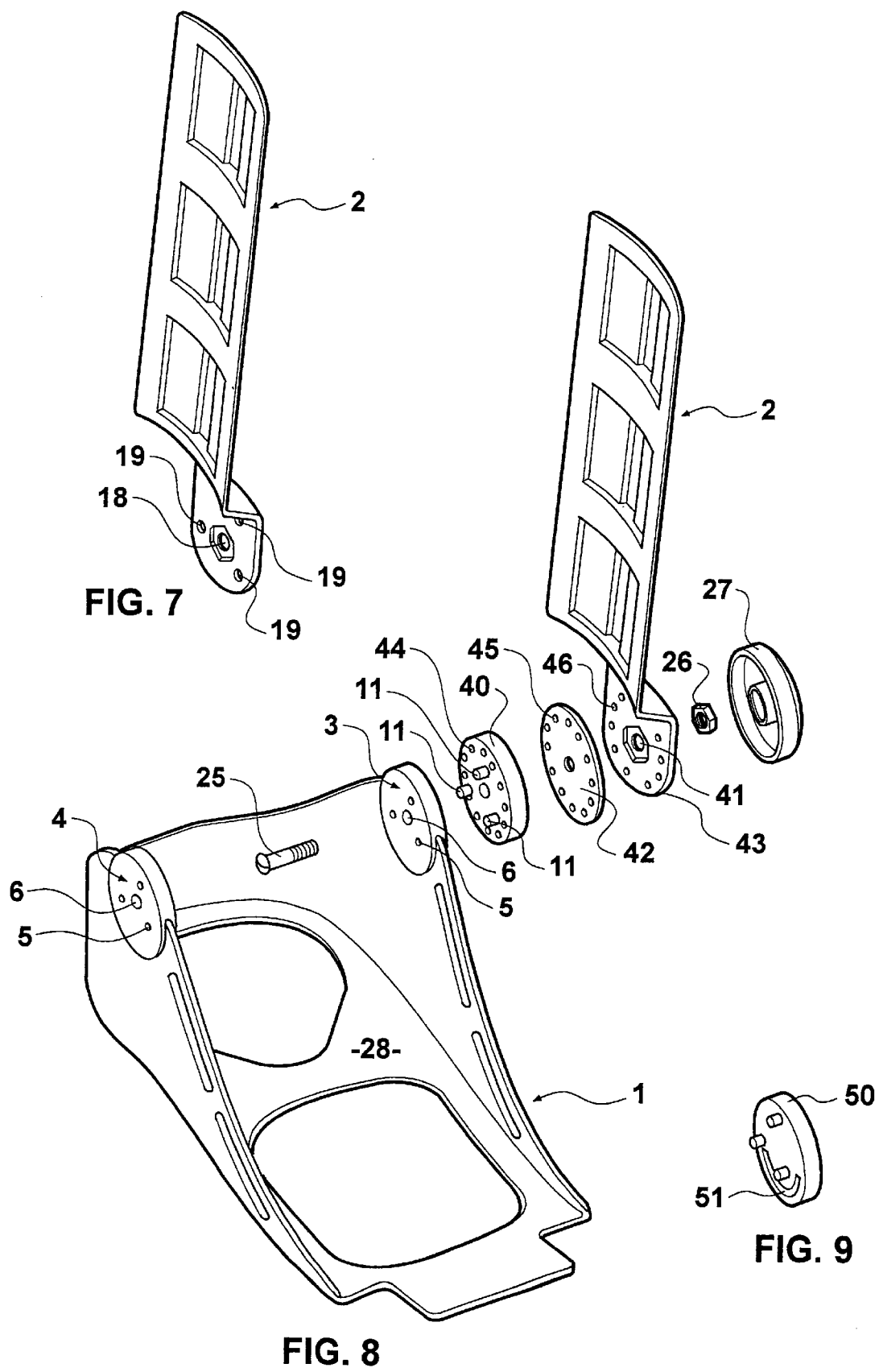

PLUG FOR CONNECTING TO A WALKER

BACKGROUND OF THE INVENTION

This invention relates to a plug for a walker.

Walkers consist of boot sections and arms. The arms are either fixed and are generally held in place by rivets or, in some constructions, the arms are attached through a range of motion mechanism. Some walkers are provided in which the arms are able to be snapped into a slot in the walker.

In any event walkers are bulky and therefore expensive to ship and also take up a lot of room in store-rooms. This is disadvantageous.

SUMMARY OF THE INVENTION

It is therefore an object of the present invention to provide a plug for a walker which will obviate or minimize the foregoing disadvantages in a simple yet effective manner or which will at least provide the public with a useful choice.

Accordingly, one aspect of the invention comprises a plug for connecting to a walker, the plug comprising a plate, an aperture in the plate and a plurality of pins extending from the plate, the pins being positioned to engage in use corresponding apertures in a walker body.

Preferably the aperture comprises a central aperture.

Preferably three pins are provided equally spaced about the aperture.

Preferably the aperture is provided at the base of a depression in the face of the plate opposite the face from which the pins extend.

Preferably walker arms are provided, the arms being provided with corresponding apertures so that the pins can pass through the apertures into the arm into the corresponding apertures in the walker body so as in use to hold the arm to the walker.

In alternative constructions the face of the plate opposite the pins has means to co-operate with a walker arm or means associated therewith to allow the walker arm to be positioned in one of a selected number of available positions or to move through a range of motion.

In a further aspect the invention consists in a walker comprising a walker body, at least one walker arm and at least one plug, the walker including at least one set of apertures to receive the pins of a plug according to any one of the preceding paragraphs, and the plug or plug and/or walker being adapted to receive a walker arm.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

One preferred form of the invention will now be described with reference to the accompanying drawings in which, FIG. 7 is a perspective view of an arm for use with the plug of FIGS. 1 to 6, FIG. 8 is an exploded perspective view of a walker utilising an alternative plug, and FIG. 9 is a diagrammatic view of a still further plug for use in the invention.

Figure 1:
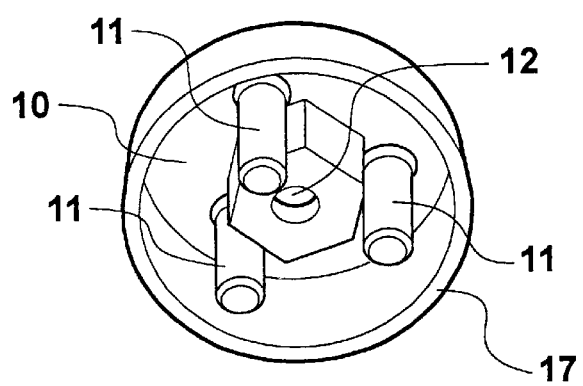
FIG. 1 is a perspective view of a plug according to one preferred form of the invention.
Figure 2:
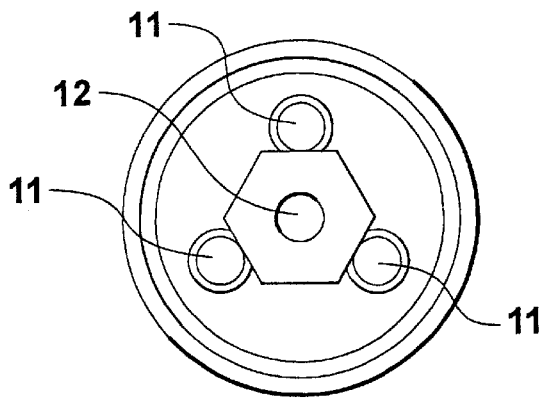
FIG. 2 is a plan view of the plug of FIG. 1.
Figure 3:
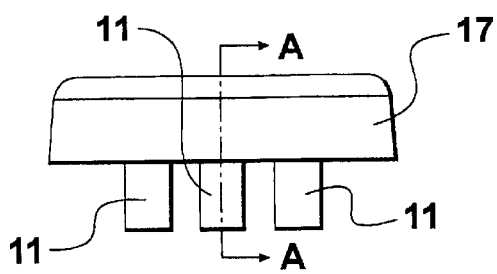
FIG. 3 is a side elevation of the plug of FIG. 1.

Referring to the drawings a plug and a walker are provided as follows.

DETAILED DESCRIPTION OF THE PREFERRED EMBODIMENTS

A walker body 1 is shown in FIG. 7 and one or more, usually two, arms 2 are able to be, or intended to be, engaged with the walker body 1. To enable two such arms to be provided regions 3 and 4 are provided on the walker body 1 which regions include a number of apertures 5 and a central aperture 6. The apertures 5 are spaced about the central aperture 6.

In the plug of FIGS. 1 to 6 a plate 10 is provided from which extend a number of pins 11. In the preferred embodiment there are three pins equally spaced about an aperture, usually a central aperture 12. The pins 11 and the apertures 5 are correspondingly positioned so that the pins 11 are positionable in the apertures 5 in use, The central aperture 12 is positioned at the, bottom face of a depression 15, the depression preferably being hexagonal in cross-sectional shape to provide flats 16 so as to enable a nut to be captured in use.

Figure 4:
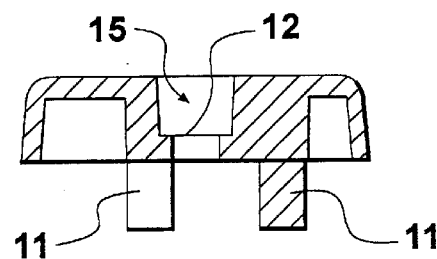
FIG. 4 is a cross-section on AA in FIG. 3.
Figure 5:
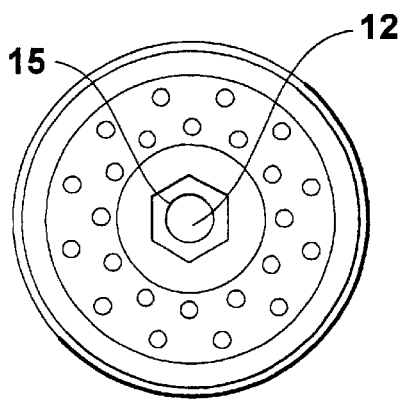
FIG. 5 is a elevation of the plug from the reverse side when compared to FIG. 2.
Figure 6:
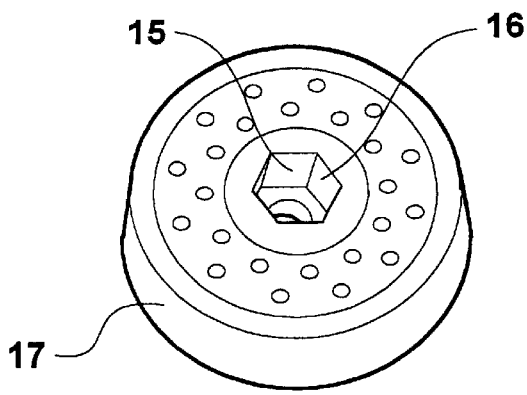
FIG. 6 is a perspective view of the face shown in FIG. 5.

The plate 10 preferably has around its periphery a skirt 17 of a length such that the pins 11 stand proud of the skirt 17 as can be seen in FIG. 4, In use a walker arm 2 is provided as shown in FIG. 7 which has a central aperture 18 and three corresponding apertures 19, so that the pins 11 can be passed through the apertures 19 and then into the apertures 5. The position of the arm is therefore fixed. The construction is then secured, for example, by a bolt 25 (shown in FIG. 8) which passes through the apertures 6 and 12, as well as the aperture 18, and is secured by a nut 26 (shown in FIG. 8) which is captured in the depression 15. Of course the nut and bolt arrangement could be reversed with the nut on the inside and the bolt entering from the outside. The particular connection method is not essential and can be varied to other secure attachment methods.

A cover such as snap on cover plate 27 (shown in FIG. 8) may be provided if desired.

Thus in this construction the walker may be initially packaged with the arms in a position such that they lie somewhat parallel to the base 28 of the walker or at least inclined inwardly towards it so as to minimise packaging or storage room. When desired the bolt 25 can be loosened, the plug and arm removed and repositioned with different pins 11 in different apertures 5 and/or 18 so that the walker arm is positioned more in the attitude shown in FIG. 8.

Referring now to FIG. 8 a plug 40 is provided which again has pins 11 as above described. The walker arm however is provided with the central aperture 41 through which the bolt 25 can pass and be secured by nut 26.

A spacing washer 42 may be provided if desired. The plug 40, the washer 42 if provided, and the parts 43 of the arm about the aperture 41 are provided with means to enable the arm to be placed in a number of positions such as corresponding depressions and protrusions indicated diagrammatically at 44, 45 and 46, or in other manners as desired such as by providing apertures at those points through which pins can be positioned.

The use of this embodiment is substantially as before save that a wider range of positions of the arm are provided. Again the arm can be folded downwardly for storage and transportation and can be moved to a selected position.

In the embodiment shown in FIG. 9 a plug 50 is provided which replaces the plug 40 and the plug 50 includes a slot 51 therethrough so that by providing a suitable pin or protrusion on the walker arm or washer the arm can be, when in the extended or assembled position, moved through a range of motion. Again, however the arms can be folded flat, either by removing the plug 50 and rotating it or if the allowable range of motion is sufficient folding the arm down forwardly.

Constructions can also be envisaged in which the pins extend outwardly from the walker body and apertures are provided in the plug.

Thus it can be seen that at least in the preferred form of the invention a plug and/or a walker are provided which have the advantage that the arms can be held secure to the walker body whilst yet allowing the arms to be readily assembled into the use position. This has the advantage that transportation and storage is simplified. The walker can be packed into a smaller space even with the arms attached.

This results in inventory management efficiencies and more management options for each patient. It is clear that constructions are available in which the fixed plug, the range of fixed position plug and the range of motion plug are interchangeable such that a walker and arm combination can be adjusted from one to the other simply by changing the plug. In such a construction the arms would be in all cases positioned to the outwardly facing face of the plug as shown in FIG. 8 rather than provided with apertures through which the pins 11 would pass.

It is a particular advantage of the construction that the product function can be varied to match the patients exact stage of rehabilitation or immobilisation. This is because the walker boots can be held separately and the required arm length and function attached as required. Thus various arm mechanisms can be used with one boot for any given patient. Thus arms are readily interchangeable. A fixed arm model can be simply converted to a range of fixed positions or a range of motion model simply by interchanging plugs.

What I claim is:

1. A plug for connecting to a walker, the plug comprising:
   a plate having a first face and a second face;
   an aperture in the plate; and
   a plurality of pins extending from the plate, the pins being positioned to engage, in use, corresponding body apertures in a walker body; and walker arms, the arms being provided with corresponding arm apertures so that the pins can pass through the arm apertures into the arm into the corresponding body apertures so as, in use, to hold the arm to the walker.

2. A plug as claimed in claim 1, wherein the aperture comprises a central aperture.

3. A plug as claimed in claim 1, wherein three pins are equally spaced about the aperture.

4. A plug as claimed in claim 1, wherein the aperture is at a base of a depression of the first face, said pins extending from the second face.

5. A plug as claimed in claim 1, wherein the first face has means to allow the walker arm to be in one of a selected number of positions.

6. A plug as claimed in claim 1, wherein the first face has means to allow the walker arm to move through a range of motion.

7. A walker comprises a walker body, at least one walker arm, and at least one plug, the walker including at least one set of apertures to receive the pins of a plug according to claim 1,
   at least one of said plug and said walker being adapted to receive a walker arm.

8. A plug for connecting to a walker that receives a wearer's foot, the plug comprising:
   a plate having a first and a second face;
   an aperture in said plate;
   a plurality of pins extending from said plate, said pins being positioned to engage, in use, corresponding body apertures in a walker body,
   said plug being engageable with the walker in at least two orientations, a first orientation being for packaging and a second orientation being for use when a foot is in the walker, and
   walker arms, the arms comprising corresponding arm apertures so said pins can pass through said arm apertures into the arm into the corresponding body apertures so as, in use, to hold the arm to the walker.

9. A walker comprises a walker body, at least one walker arm, and at least one plug, the walker including at least one set of apertures to receive pins of a plug, said plug comprising:
   a plate having a first and a second face;
   an aperture in said plate;
   a plurality of said pins extending from said plate, said pins being positioned to engage, in use, corresponding body apertures in a walker body,
   said plug being engageable with the walker in at least two orientations, a first orientation being for packaging and a second orientation being for use when a foot is in the walker, and
   at least one of said plug and said walker being adapted to receive a walker arm.

* * * * *